United States Patent [19]

Fetty et al.

[11] Patent Number: 4,716,180

[45] Date of Patent: Dec. 29, 1987

[54] COMPOSITION AND METHOD FOR THE PRESERVATION OF MASTITIS

[75] Inventors: Walter Fetty, Lincoln, Nebr.; Joseph R. Killian, Akron, Ohio

[73] Assignee: Killian Latex, Inc., Akron, Ohio

[21] Appl. No.: 672,486

[22] Filed: Nov. 16, 1984

[51] Int. Cl.$^4$ .............................................. A01N 25/00
[52] U.S. Cl. ..................................................... 514/782
[58] Field of Search .......................................... 514/782

[56] References Cited

U.S. PATENT DOCUMENTS

| | | | |
|---|---|---|---|
| 2,604,092 | 7/1952 | Brown et al. | 128/132 R |
| 3,066,071 | 11/1962 | Akers et al. | 424/78 |
| 3,222,252 | 12/1965 | Kraus | 514/390 |
| 4,022,199 | 5/1977 | Fetty | 128/132 R |
| 4,113,854 | 9/1978 | Andrews et al. | 424/81 |

OTHER PUBLICATIONS

*Rubber Developments*, "Teat Dip Aids Dairy Farmers", vol. 38, No. 2, pp. 39-41, 1985.

*Primary Examiner*—Douglas W. Robinson
*Assistant Examiner*—John M. Kilcoyne
*Attorney, Agent, or Firm*—Low and Low

[57] ABSTRACT

A composition and method are provided for preventing mastitis in milk producing animals. The composition comprises natural rubber latex, propylene glycol and is applied to the teat of the milk producing animal to form a protective, pliable film.

6 Claims, No Drawings

COMPOSITION AND METHOD FOR THE PRESERVATION OF MASTITIS

BACKGROUND OF THE INVENTION

In the milk producing industry maintaining the animals in disease free condition is a primary concern. Mastitis, an inflammation of the mammary gland, usually caused by a bacterial infection, is of particular concern as it can lead to decreased milk productivity, complete loss of milk, and even eventual destruction of the animal.

Despite the enforced sanitation requirements of the milking process, such as providing for cleaning the animals' teats prior to milking, diseases like mastitis can easily spread through an entire herd from a single infected animal. As the infected animal mingles with healthy animals, as while grazing in the field, bacteria may be spread from animal to animal by insects, by contact with grass which has been contaminated by contact with the infected animal, and the like.

While mastitis can be treated with antibiotics and by prophylactic disinfectants and other drugs, before the infected animal can be isolated for treatment thus protecting the remaining animals from contamination, the bacteria usually has spread to healthy animals. Thus, there is a need for a method of preventing healthy livestock from contacting the bacteria from the infected specimens.

The need for prevention of the spread of bacteria is recognized in U.S. Pat. No. 2,604,092 to Brown et al, where bulbous sheaths of flexible elastic material are adhesively secured at the neck to the teats of the cows. The sheaths, however, must be laboriously removed before cleaning the teats and milking and then must be replaced, requiring a substantial investment of time.

Several attempts to provide protective film barriers on the teats have been made. U.S. Pat. No. 3,066,071 to Akers et al teaches a method of coating the teats of cattle with a peelable film of a mixture of polyvinyl acetate and polyvinyl chloride, typically applied from a volatile solvent such as ethyl acetate or as a hot melt. The resulting disadvantages can be significant; the skin of the teat can be irritated by the effects of the solvent or by the heat of the melt composition.

U.S. Pat. No. 3,222,252 to Kraus describes a bovine teat dip consisting of certain fatty acid esters and drying or semi-drying vegetable oils. However, the vegetable oil dips are difficult to remove from the animal's teats with a water wash, and are ineffective in preventing mastitis.

U.S. Pat. No. 4,022,199 to Fetty is directed to a method for mastitis prevention comprising covering the teat with a mucilage gum to form a protective film on the teat.

U.S. Pat. No. 4,113,854 to Andrews teaches a method for preventing mastitis comprising dipping the animals' teats into a composition comprising a film-forming polymer, specifically a synthetic (acrylic) latex, and a water soluble thickening agent, and the composition thereof. However, the dip composition is permanently damaged upon freezing, and cannot be effectively used again after thawing.

SUMMARY OF THE INVENTION

It is an object of the invention to overcome the disadvantages of prior art methods for control of mastitis, and to provide an effective means for its control.

It is another object of the invention to develop a method and composition which is simple and economical to use by dairy herd management.

It is a further object to provide a method and composition for the control of mastitis which causes no discomfort to the animal and which does not interfere with the normal milking process.

It is a further object of the invention to provide a method for control of mastitis where the composition employed is not deleteriously affected by temperatures below freezing.

The present invention provides a solution to the need for an effective deterrent to the spread of mastitis and overcomes the disadvantages of prior methods. The further objects, advantages and novel features of the invention will become apparent from the description below.

DESCRIPTION OF THE PREFERRED EMBODIMENT

The present invention provides both a composition and a method for preventing the contamination of healthy dairy animals with mastitis-causing bacteria.

The mastitis prevention composition of the present invention comprises a natural rubber latex propylene glycol mixture.

Essential to the composition is the inclusion of propylene glycol along with the natural rubber latex, which permits the liquid to withstand exposure to temperatures below 32° F., without deleterious effects. After the solution is frozen, exposure to temperatures above 32° F. will cause the solution to liquify to normal consistency, whereupon it may simply be stirred and applied to the animals in the normal fashion, requiring no special equipment for the preserving or maintenance of the composition in cold climates.

The composition includes fillers and pigments so that the film is visible against the skin of the animal, providing a simple visual means for checking that every animal has been protected by the diary personnel and conversely, that the film has been removed prior to milking. Such fillers include titanium dioxide and clay.

The composition further includes vulcanizing agents stabilizers, anti-bacterial agents, suspension agents, and perfume.

Suitable vulcanizing agents include sulphur, while sodium isopropyl xanthate and mercaptobenzothiazole serve as precure accelerators. Suggested stabilizers include potassium hydroxide, caustic soda, sulfonated fatty acid, ammonia, casein, oleic acid, shellac, triethanolamine, and diethylamine and wax for ozone protection.

Suitable dispersing agents may include sodium salts of alkyl sulfonic acid, sodium alkyl arylether sulfate with shellacol alcohol as the dispersing agent.

Suggested antibacterial agents are para-chloro meta xylenol and sodium-ortho phenylphenate tetrahydrate.

The composition is nonirritating to the skin of the animal's teat, and is easy to apply and remove. The composition may be applied to the teat by dipping, spraying or brushing onto the animal forming a continuous protective film over the teat and across the orifice of the teat, and after drying of the composition protecting the teat from the entrance of bacteria and from the deleterious effects of exposure to environmental factors. The latex film lasts from milking to milking without easily being rubbed off by the animal, yet is removed by the dairy personnel with warm water just prior to milking.

As will be evident from the relative weights shown in the best mode of the invention set forth with particularity hereinafter, it will be seen that the subject composition contemplates rubber latex as a chief ingredient and forming a major proportion thereof on the order of about 50% by weight, along with about 6% propylene glycol as a second major constituent (apart from water to about 38% by weight), and which with the water form a minor proportion of the composition as compared to the latex.

Vulcanizing agents and precure accelerators therefor form only a quite small fraction, together about 0.33% by weight and wherein the vulcanizing agent proper is a minor portion thereof, or about 0.13% of the total. Similarly, fillers and pigments for ready visibility are present to about 3.1% by weight.

BEST MODE FOR CARRYING OUT THE INVENTION

|  | Wt in Lbs |
|---|---|
| Natural Rubber Latex (dry weight) | 4162.5 |
| Propylene Glycol | 500. |
| Sulfur | 10.4 |
| Perfume | 13.0 |
| Aero-Xanthate (American Cyanamid Sodium Isopropyl Xanthate) | 4.2 |
| Zetax (RT Vanderbilt mercaptobenzothiazole) | 12.4 |
| Titanium Dioxide | 165.62801 |
| Polyplate P (Clay-Huber Clay Co.) | 83.2 |
| Green Pigment | 9.0 |
| Versene 100 (Dow Chemical Tetrasodium Salt of Ethylene diamine tetraacetic acid) | 30.0 |
| KOH (potassium hydroxide) | 29.274302 |
| Modicol S (Diamond Shamrock Co. - Sulfonated fatty acids) | 16.5 |
| Casein | 6.0016 |
| Wax | 8.042235 |
| Gum Arabic | 6.79152 |
| Ammonia | 6.53200444 |
| Emersol Elaine 210 (Emery Industries - Oleic Acid) | 0.8064662 |
| Ottasept Tech 101 (Ferro Ottowa - Parachloro meta-xylenol) | 11.6428034 |
| Darvan #1 (RT Vanderbilt Co.-Sodium Salt of Alkyl Sulfonic Acid) | 1.68 |
| Shellac | 0.6057692 |
| Shellacol Alcohol | 0.6057692 |
| Triethanolamine | 0.3216894 |
| Triton No. 770 (Sodium Aklyl Arylether Sulfate) | 0.3216894 |
| Diethylamine | 0.234233 |
| Caustic Soda | 0.2085552 |
| Downside Flake (Dow Chemical - Sodium o-phenylphenate tetrahydrate) | 0.2085552 |
| Water | 3,119.8948017 |
|  | 8,200.000 lbs |

The composition is prepared by dispersing the ingredients, then mixing them together. The mixture is heated to 160° F. then cooled to 75° F. In the heating process, the necessary cross-linking is achieved to make the material suitable for its use as a protective film.

What I claim is:

1. A liquid film-forming composition for the preventative treatment of mastitis in dairy animals by application thereof onto a teat, comprising in substantially the following weight ratios:

| 4162.50 wt. | natural rubber latex |
|---|---|
| 500.00 wt. | propylene glycol |
| 10.40 wt. | sulfur |
| 4.20 wt. | sodium isopropyl xanthate |
| 12.40 wt. | mercaptobenzothiazole |
| 83.20 wt. | clay |
| 30.00 wt. | tetrasodium salt of ethylenediamine tetraacetic acid |
| 29.27 wt. | potassium hydroxide |
| 16.50 wt. | sulfonated fatty acid |
| 6.00 wt. | casein |
| 8.04 wt. | wax |
| 6.79 wt. | gum Arabic |
| 6.53 wt. | ammonia |
| .81 wt. | oleic acid |
| 11.64 wt. | parachloro meta-xylenol |
| 1.68 wt. | sodium salt of alkyl sulfonic acid |
| .61 wt. | shellac |
| .61 wt. | alcohol |
| .32 wt. | triethanolamine |
| .32 wt. | sodium alkyl arylether sulfate |
| .21 wt. | caustic soda |
| .21 wt. | sodium o-phenylphenate tetrahydrate, and, |
| 3119.89 wt. | water. |

2. A method for the preventive treatment of mastitis in dairy animals comprising the steps of dipping, spraying or brushing onto the teats of the animal a liquid composition having substantially the following weight ratios:

| 4162.50 wt. | natural rubber latex |
|---|---|
| 500.00 wt. | propylene glycol |
| 10.40 wt. | sulfur |
| 4.20 wt. | sodium isopropyl xanthate |
| 12.40 wt. | mercaptobenzothiazole |
| 83.20 wt. | clay |
| 30.00 wt. | tetrasodium salt of ethylenediamine tetraacetic acid |
| 29.27 wt. | potassium hydroxide |
| 16.50 wt. | sulfonated fatty acid |
| 6.00 wt. | casein |
| 8.04 wt. | wax |
| 6.79 wt. | gum Arabic |
| 6.53 wt. | ammonia |
| .81 wt. | oleic acid |
| 11.64 wt. | parachloro meta-xylenol |
| 1.68 wt. | sodium salt of alkyl sulfonic acid |
| .61 wt. | shellac |
| .61 wt. | alcohol |
| .32 wt. | triethanolamine |
| .32 wt. | sodium alkyl arylether sulfate |
| .21 wt. | caustic soda |
| .21 wt. | sodium o-phenylphenate tetrahydrate, and, |
| 3119.89 wt. | water, and, | permitting the composition to dry on the teat to form a protective film thereover.

3. The composition of claim 1 further including titanium dioxide in the ratio of substantially 165.63 by weight and coloring pigment in the ratio of substantially 9.0 by weight to enhance the visual appearance of the composition.

4. The composition of claim 3 further including a perfume in the ratio of substantially 13.00 by weight to enhance the odor of the composition.

5. The method of claim 2 wherein the composition further includes titanium dioxide in the ratio of substantially 165.63 by weight and coloring pigment in the ratio of substantially 9.0 by weight to enhance the visual appearance of the composition.

6. The method of claim 5 wherein the composition further includes perfume in the ratio of substantially 13.00 by weight to enhance the odor of the composition.

* * * * *